United States Patent [19]

Hamilton

[11] Patent Number: 5,426,114
[45] Date of Patent: Jun. 20, 1995

[54] ω-[2-(TETRAZOLYLALKYL)CYCLOHEXYL]-2-AMINOALKANOIC ACIDS AS ANTAGONISTS OF EXCITATORY AMINO ACID RECEPTORS

[75] Inventor: Gregory S. Hamilton, Catonsville, Md.

[73] Assignee: Guilford Pharmaceuticals Inc., Baltimore, Md.

[21] Appl. No.: 245,162

[22] Filed: May 17, 1994

Related U.S. Application Data

[62] Division of Ser. No. 984,454, Dec. 2, 1992, Pat. No. 5,331,001.

[51] Int. Cl.$^6$ ............................................. A61K 31/41
[52] U.S. Cl. ....................................................... 514/381
[58] Field of Search ........................................ 514/381

[56] References Cited

U.S. PATENT DOCUMENTS

| | | | |
|---|---|---|---|
| 4,657,899 | 4/1987 | Rzeszotarski et al. | 514/120 |
| 4,761,405 | 8/1988 | Rzeszotarski et al. | 514/114 |
| 4,822,780 | 4/1989 | Tsuda et al. | 514/119 |
| 4,918,064 | 4/1990 | Cordi et al. | 514/114 |
| 5,049,555 | 9/1991 | Rzeszotarski et al. | 514/114 |
| 5,331,001 | 7/1994 | Hamilton | 514/381 |

FOREIGN PATENT DOCUMENTS 432994 6/1991 European Pat. Off. .

OTHER PUBLICATIONS

Watkins et al., "Excitatory Amino Acid Transmitters," *Amer. Rev. Pharmacol. Toxicol.* (1981), vol. 21, pp. 165–204.

Schwarcz et al., "Quinolinic Acid: An Endogenous Metabolite that Produces Axon-Sparing Lesions in Rat Brain," *Science*, Jan. 1983, vol. 219, pp. 316–318.

Simon et al., "Blockade of N-Methyl-D-Aspartate Receptors May Protect Against Ischemic Damage in the Brain," *Science*, vol. 226, pp. 850–852 (1983).

Foster et al., "Acidic Amino Acid Binding Sites in Mammalian Neuronal Membranes: Their Characteristics and Relationship to Synaptic Receptors," *Brain Research Reviews*, vol. 7, (1984), pp. 103–164.

Schoepp et al., "Pharmacological and Functional Characteristics of Metabotropic Excitatory Amino Acid Receptors," *Tr. Pharmacol. Sci.*, Special Report (1991), pp. 74–81.

Faden et al., "Effects of Competitive and Non≧Competitive NMDA Receptor Antagonists in Spinal Cord Injury," *European Journal of Pharmacology*, vol. 175 (1990), pp. 165–174.

Frandsen et al., "Direct Evidence that Excitotoxicity in Cultured Neurons is Mediated via N-Methyl-D-Aspartate (NMDA) as well as Non-NMDA Receptors," *Journal of Neuro-Chemistry*, vol. 53, No. 1, 1989, pp. 297–299.

Sheardown et al., "2,3-Dihydroxy-6-nitro-7-sulfamoyl-benzo(F)quinoxaline: A Neuroprotectant for Cerebral Ischemia," *Science*, vol. 247, Feb. 1990, p. 571.

Costa, "Allosteric Modulatory Centers of Transmitter Amino Acid Receptors," *Neuropsychopharmacology*, vol. 2, No. 3, (1989), pp. 167–174.

Matoba et al., "Structural Modification of Bioactive Compounds. II. Syntheses of Aminophosphonoic Acid," *Chem. Pharm. Bulletin*, vol. 32 (1984), pp. 3918–3925.

Lodge et al., [Eds.], "The Pharmacology of Excitatory Amino Acids," *Elsevier Trends Journal* (1991).

*Primary Examiner*—Raymond Henley, III
*Attorney, Agent, or Firm*—Nath, Amberly & Associates; Gary M. Nath

[57] ABSTRACT

The present invention pertains to antagonists of excitatory amino acid receptors, their method or preparation as well as compositions pertaining to them, which have the general formula:

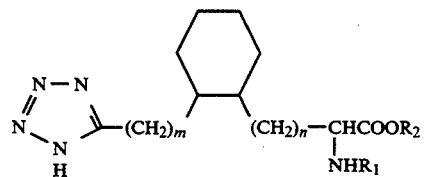

wherein R1 and R2 are selected from the group of hydrogen and C1 to C6 lower alkyl; the stereoisomers being in their resolved or racemic form; n and m are independently 0, 1, 2, or 3; and pharmaceutically acceptable salts thereof.

16 Claims, No Drawings

ω-[2-(TETRAZOLYLALKYL)CYCLOHEXYL]-2-AMINOALKANOIC ACIDS AS ANTAGONISTS OF EXCITATORY AMINO ACID RECEPTORS

This application is a division of U.S. patent application Ser. No. 07/984,454, filed Dec. 2, 1992 now U.S. Pat. No. 5,331,001.

BACKGROUND OF THE INVENTION

1. Field of the Invention

The present invention pertains to novel excitatory amino acid (EAA) receptor antagonists and particularly to novel, potent and selective antagonists of the N-methyl-D-aspartate (NMDA) subset of EAA receptors having anxiolytic, anticonvulsant, antiepileptic, analgesic, antiemetic, neuroprotective and cognition enhancing actions achieved through the antagonisms of these receptors. In particular, the invention is directed to: ω-[2-(tetrazolylalkyl) cyclohexyl-2-aminoalkanoic acids and their interaction with NMDA receptors, their pharmaceutically acceptable salts, and uses thereof.

2. Description of the Prior Art

Excitatory amino acids (EAAs) mediate a substantial portion of the chemical synaptic activity occurring in the central nervous system. Current understanding recognizes at least three major ionotropic receptors for EAAs. Most commonly identified by prototypical agonists, these include:

(1) receptors activated by AMPA [(R,S)-α-aminomethyl-3-hydroxy-5-methylisoxazolpropionic acid], a cyclic analog of L-glutamate (GLU), (2) receptors recognizing the pyrrolidine neurotoxin kainic acid (KA), and (3) receptors responding to N-methyl-D-aspartate (NMDA), a synthetic analog of L-aspartate [D. R. Curtis, A. W. Duggar, D. Felix, G. A. R. Johnston, A. K. Tebecis and J. C. Watkins, Brain Res., 41, 283-301 (1972); J. C. Watkins and R. H. Evans, Ann. Rev. Pharmacol. Toxicol., 21, 165-204 (1981); A. C. Foster and G. Fagg, Brain Res. Rev., 7, 103-164 (1984)]. In addition to these major ion channel-linked receptors, evidence now suggests the presence of metabotropic EAA receptors which directly activate second messenger systems [D. Schoepp, J. Brockaert and F. Sladeczek, In C. Lodge and G. L. Collinridge (eds.) Tr. Pharmacol. Sci., Special Report, "The Pharmacology of Excitatory Amino Acids," Elsevier, Cambridge, UK, pp 74-81 (1991)]. Furthermore, it is now apparent that the NMDA-mediated ionotropic responses are subject to complex regulatory influences and, that this particular recognition site may exist as a supramolecular entity similar to the GABA/benzodiazepine/barbituate effector proteins [E. Costa, Neuropsychophramacology, 2, 167-174 (1989)].

In general, EAA agonists are potent convulsants in an animal model. Additionally, AMPA, KA and the endogenous NMDA agonist, quinolinic acid (QUIN) and the mixed ionotropic/metabotropic against ibotenic acid have been used to produce laboratory models of neurodegenerative disorders [K. Biziere, J. T. Slevin, R. Zaczek, J. S. Collins and J. T. Coyle. In H. Yoshida, Y. Hagihara and S. Ebashi (eds.), "Advances in Pharmacology and Therapeutics," New York: Pergamon, 1982, 271-276; R. Schwarcz, E. O. Whetsell and R. M. Mango, Science, 219, 316-318 (1983)]. It has been suggested for some time that a dysfunction in EAA neurotransmission may contribute to the neuropathology associated with the epilepsies and neurodegenerative conditions [B. Meldrum and M. Williams (eds.), "Current and Future Trends in Anticonvulsant, Anxiety and Stroke Therapy," New York: Wiley Liss, 1990].

The development of selective NMDA antagonists has further expanded the understanding of EAA neurotransmission, physiology and pathophysiology in the mammalian brain. In particular, substantial preclinical evidence is now available suggesting that NMDA receptor antagonists may be useful as anxiolytics, anticonvulsants, antiemetics, antipsychotics or muscle relaxants, and that these compounds may prevent or reduce neuronal damage in instances of cerebral ischemia, hypoxia, hypoglycemia or trauma [R. P. Simon, J. H. Swan, T. Griffiths and B. S. Meldrum, Science, 226, 850-852 (1984); D. N. Stephens, B. S. Meldrum, R. Weidman, C. Schneider and M. Grutzner, Psychopharmacology, 90, 166-169 (1986); D. Lodge and G. L. Collinridge (eds.) "The Pharmacology of Excitatory Amino Acids,"Elsevier Trends Journals, Cambridge, UK (1991); A. I. Fader, J. A. Ellison and L. J. Noble, Eur. J. Pharmacol., 175, 165-174 (1990)].

Given the broad therapeutic potential of EAA antagonists, it is not surprising that efforts have been initiated to identify antagonist compounds. The advent of potent and selective antagonists of EAAs, exemplified by α-amino-ω-phosphonoalkylcarboxylic acids has provided a point of departure for the pharmacologic intervention of EAA action at their receptors [J. C. Watkins, Can. J. Physiology Pharmacol., 69, 1064-1076 (1991)]. Although the requisite ω-acidic group has most often been a phosphonic acid moiety, recent examples from the literature suggest that a tetrazole functionality can, in some instances, substitute for the phosphono group with a retention of NMDA antagonist activity. Thus, the compounds cis-4-tetrazolylmethyl-piperidine-2-carboxylic acid [P. L. Ornstein, D. E. Schoepp, M. B. Arnold, J. D. Leander, D. Lodge, J. W. Paschal and T. Elzey, J. Med. Chem., 34, 90-97 (1991); P. L. Ornstein et al., U.S. Pat. No. 4,902,687] and decahydro-6-[1(2H)-tetrazol-5-ylmethyl]-3-isoquinolinecarboxylic acid [P. L. Ornstein et al., U.S. Pat. No. 4,902,695]have been reported to be potent and selective NMDA antagonists which are characterized by a shorter duration of action than in the case of the corresponding phosphonic acids. It should be noted that substitution of other monoacidic isosteres for the phosphono acid moiety in similar compounds (e.g., carboxylate or sulfonate) results in abolition of antagonist activity.

SUMMARY OF THE INVENTION

The present invention provides an excitatory amino acid neurotransmitter receptor antagonist having the general formula:

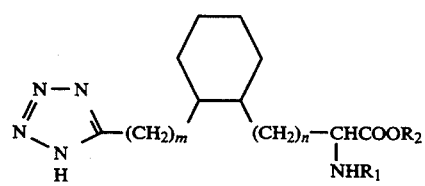

wherein R1 and R2 are selected from the group consisting of hydrogen and C1 to C6 lower alkyl; the stereoisomers being in their resolved or racemic form; n and m are independently 0, 1, 2, or 3; and pharmaceutically acceptable salts thereof.

The invention also provides as an alternate embodiment a method for antagonizing excitatoryamino acid NMDA receptors by utilizing compounds having the general formula:

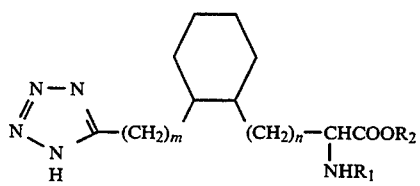

Wherein R1 and R2 are selected from the group consisting of hydrogen and C1 to C6 lower alkyl; the stereoisomers being in their resolved or racemic form; n and m are independently 0, 1, 2, or 3; and the pharmaceutically acceptable salts thereof.

Another aspect of the invention involves use of the pharmaceutical compositions in a method for relieving pain, treatment of convulsions or epilepsy, enhancing cognition, treating psychosis, preventing neurodegeneration, treating cerebral ischemia or traumainduced damage, and treating emesis.

In another embodiment, the invention involves the formation of specific compounds, including:
3-[2-[2-(2H)-tetrazol-5-ylethyl]cyclohexyl]alanine;
3-[2-[2-(2H)-tetrazol-5-ylethyl]cyclohexyl]-N-methylalanine;
3-[2-[2-(2H)-tetrazol-5-ylethyl]cyclohexyl]alanine, ethyl ester;
(2R, 4R, 5S)-3-[2-[2-(2H)-tetrazol-5-ylethyl]cyclohexyl]alanine;
(2R, 4R, 5S)-3-[2-[2-(2H)-tetrazol-5-ylethyl]cyclohexyl]-N-methylalanine; and
(2R, 4R, 5S)-3-[2-[2-(2H)-tetrazol-5-ylethyl]cyclohexyl]alanine, ethyl ester.

DETAILED DESCRIPTION OF THE INVENTION

The structure and formulation of the novel compounds of the invention was the result of an extensive research investigation into the antagonism of heterogenic EAA neurotransmitter receptors.

It is generally accepted that L-glutamic acid (GLU), a dicarboxylic amino acid is the principal excitatory amino acid neurotransmitter in the vertebrate central nervous system (CNS). Ion-channel linked or "ionotropic" excitatory amino acid receptor subtypes include those selectively activated by N-methyl-D-aspartate (NMDA), α-amino-3-methyl-4-isoxazolepropionic acid (AMPA), and kainic acid (KA). A metabotropic GLU receptor coupled to phospholipid metabolism and a putative GLU autoreceptor have also been identified. L-glutamate is believed to have an important physiological role in the functioning of the CNS since a great majority of CNS neurons utilize GLU as their neurotransmitter.

In addition, the diversity of receptor subtypes with which GLU interacts contributes to its ability to elicit a variety of synaptic events. Ionotropic GLU receptors mediate fast excitatory postsynaptic potentials and contribute to the architectural development and plasticity of excitatory synapses. Metabotropic GLU receptors are considered to play primarily a neuromodulatory role, although simultaneous activation of ionotropic and metabotropic receptors might be required for the development of neuronal plasticity at certain CNS synapses.

Because of its involvement in excitatory neurotransmission, GLU has been suggested to have a role in CNS conditions characterized by heightened neuronal activity or sensitivity including epilepsy, ischemia or trauma-induced neuronal damage, and certain neurologic and neurodegenerative disorders. Accordingly, pharmacological manipulation of GLU receptors is therapeutically useful in the treatment of several CNS disorders and diseases.

The NMDA receptor is the most well-characterized GLU receptor subtype because of the availability of selective antagonists. D-(−)-2-amino-5-phosphonopentanoic acid (AP-5) and D-(−)-2-amino-7-phosphonoheptanoic acid (AP-7) were among the first NMDA antagonists identified that act competitively by binding to the GLU recognition site. Using these protypical antagonists as templates, several more potent and selective competitive antagonists of NMDA receptors have been developed, including 4-(3-phosphonopropyl) piperazine-2-carboxylic acid (a product of Sandoz Pharmaceuticals Corporation), cis-4-pent-3-enoic acid (a product of CIBA Pharmaceutical Company), decahydro-6-phosphonomethyl-3-isoquinolinecarboxylicacid (a product of Eli Lilly and Company) and 3-[2-(2phosphonoethyl) cyclohexyl]alanine (a product of Scios Nova Inc.).

The compounds of the present invention comprise a class of compounds in which the phosphonic acid moiety of the AP-7 template has been replaced with a tetrazole ring. Tetrazoles are known to be bioisosteres of carboxylic acids; however, replacement of the phosphonic acid group in NMDA antagonists with carboxylate or sulfonate groups results in loss of antagonist activity and frequently, manifestation of agonist activity. It has been surprisingly discovered, however, that replacement of the phosphonic acid group with an isosteric substitute can result in retention of antagonist activity. The compounds of the present invention manifest a different time course of action than the corresponding phosphonic acids, which again may render them superior for certain therapeutic indications.

Preferred compounds of the invention have the formula:

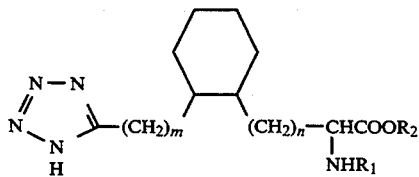

Wherein R1 and R2 are selected from the group consisting of hydrogen or C1 to C6 lower alkyl; the stereoisomers being in their resolved or racemic form; n and m are independently 0, 1, 2, or 3; and the pharmaceutically acceptable salts thereof.

A particularly preferred form of the invention has the formula:

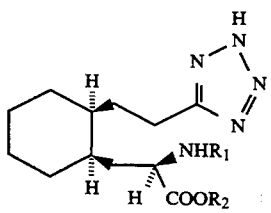

wherein R1 and R2 are selected from the group consisting of hydrogen or C1 to C6 lower alkyl; the stereochemical configuration of the compound specified as being of the (2R, 4R, 5S) configuration.

Particularly preferred specific compounds include:
3-[2-[2-(2H)-tetrazol-5-ylethyl]cyclohexyl]alanine;
3-[2-[2-(2H)-tetrazol-5-ylethyl]cyclohexyl]-N-methylalanine;
3-[2-[2-(2H)-tetrazol-5-ylethyl]cyclohexyl]alanine, ethyl ester;
(2R, 4R, 5S)-3-[2-[2-(2H)-tetrazol-5-ylethyl]cyclohexyl]alanine;
(2R, 4R, 5S)-3-[2-[2-(2H)-tetrazol-5-ylethyl]cyclohexyl]-N-methylalanine; and
(2R, 4R, 5S)-3-[2-[2-(2H)-tetrazol-5ylethyl]cyclohexyl]alanine, ethyl ester.

The preparation of the compounds for administration in pharmaceutical preparations may be accomplished in a variety of ways well known to those of ordinary skill in the art of synthetic organic chemistry. Non-limiting examples of appropriate pharmaceutically acceptable salts within the scope of the invention include those derived from mineral acids such as hydrochloric acid, phosphoric acid, hydrobromic acid and sulfuric acid, as well as organic acids such as tartaric acid, methanesulfonic acid, benzenesulfonic acid, p-toluenesulfonic acid, and the like, giving respectively the hydrochloride, phosphate, hydrobromide, sulfate, tartrate, methanesulfonate, benzenesulfonate, p-toluenesulfonate, and the like, or those derived from bases such as suitable organic and inorganic bases. Non-limiting examples of suitable inorganic bases for the formulation of salts of the compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the preparation of pharmaceutically acceptable base addition salts with compounds of the present invention include organic bases which are nontoxic and strong enough to form such salts. These organic bases form a class whose limits are clearly understood by those skilled in the art. Merely for the purposes of illustration, the class may be said to include mono-, di-, and trialkylamines, such as methylamine, dimethylamine and triethylamine; mono-, di-, and trihydroxyalkylamines such as mono-, di-, and triethanolamine; amino acids such as arginine and lysine; guanidine; N-methyl-D-glucosamine; N-methylglucamine; L-glutamine; N-methyl piperazine; morpholone, ethylenediamine; N-benzylphenethylamine; tris(trihydroxymethyl)aminomethane; and the like.

The compounds of the invention contain an asymmetric carbon atom. Thus, the invention includes individual stereoisomers, and mixtures thereof. The individual isomers may be prepared or isolated by methods known to those of ordinary skill in the art of synthetic organic chemistry.

In parenteral administration of the novel compounds and compositions of the invention, the compounds may be formulated in aqueous injection solutions, which may contain antioxidants, buffers, bacteriostats, and other conventional pharmaceutical excipients. Extemporaneous injection solutions may be prepared from sterile pills, granules or tablets which may contain diluents, dispersing and surface active agents, binders, and lubricants as well as other pharmaceutical processing aids.

In the case of oral administration, fine powders or granules of the compounds may be formulated with diluents and dispersing and surface active agents in water or in a syrup, in capsules or cachets, in the dry state, or in a non-aqueous suspension, where a suspending agent may be included. The compounds may also be administered in a tablet form along with optional binders and lubricants, or in a suspension in water or syrup, an oil or in a water/oil emulsion and may include flavoring, preserving, suspending, thickening and emulsifying agents. The granules or tablets for oral administration may be coated and other pharmaceutically acceptable agents and formulations may be utilized to which are well known to those of ordinary skill in the art.

The following examples are illustrative of preferred embodiments of the invention and are not intended to be construed as limiting the invention thereto. All percentages are based upon the weight of the final formulation unless otherwise indicated and the weight of all formulations totals 100% by weight.

The novel compounds of the invention may readily be prepared by the following synthetic routes:

(+)-(1S, 6R)-8-cis-oxabicyclo[4.3.0]non-3-en-7-one (1) may be prepared by the known methods.

Scheme I.

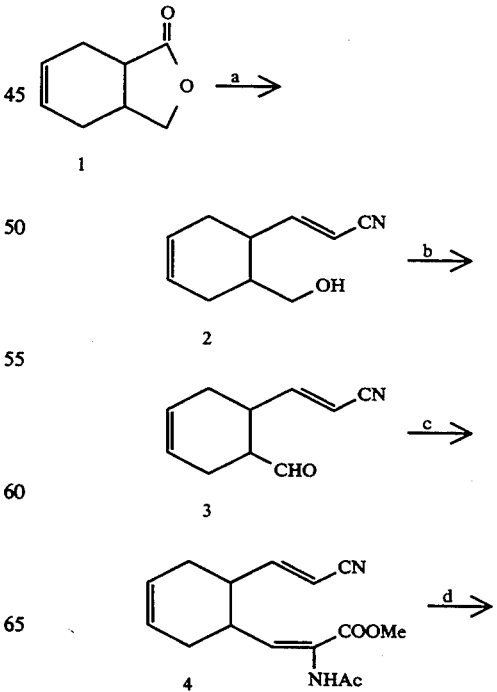

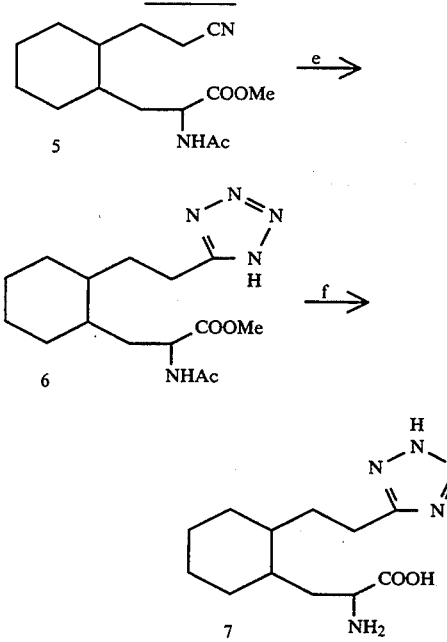

a). i: diisobutylaluminum hydride, toluene, −78° C.; ii: NaCH(CN)PO₃Et₂, tetrahydrofuran (THF)
b). pyridinium chlorochromate, CH₂Cl₂
c). sodio methyl 2-acetylamino-2-(dimethoxyphosphinyl)-acetate, THF
d). H₂, 5% Pd/C
e). nBu₃SnN₃, 80° C.
f). 6N HCl, reflux

PREPARATION I-SCHEME I

Procedure for the Synthesis of Vinyl Nitrile 2:

A solution of lactone 1 (10 mmol) in toluene (15 ml) is cooled to −78° C. and treated with 1 equivalent of diisobutylaluminum hydride in toluene (10 ml of a 1.0M solution). After stirring this mixture for 1 hour, it is added by a canula to a stirred mixture of the sodium salt of diethyl cyanomethylphosphonate (11 mmol) in THF (25 ml) at −78° C. The reaction mixture is stirred for 16 hours while allowing it to come to room temperature (24° C). It is quenched by the addition of saturated ammonium chloride (50 ml) and extracted into 2×50 ml of ethyl acetate. The organic layers are washed once with 100 ml of brine, dried (MgSO₄) and concentrated. The crude material is purified on a flash column, eluting with 20% ethyl acetate in hexane, to obtain the product.

Procedure for the Synthesis of Aldehyde 3:

A solution of pyridine-sulfur trioxide complex (5 mmol) in DMSO (50 ml) is added to a cooled (0° C.) mixture of alcohol 2 (15 mmol) and triethylamine (60 mmol) in 50 ml of DMSO. The resulting mixture is stirred for 5 hours, at which point it is poured into 200 ml of ice-water and extracted into 3×100 ml of ethyl acetate. The combined organic layers are washed with 5×50 ml of brine, dried (MgSO₄) and concentrated in vacuo. The crude product is purified on a silica gel column, eluting with 40% ether in hexane, to obtain aldehyde 3.

Procedure for the Synthesis of Dehydro Amino Acid 4:

A solution of methyl 2-acetylamino-2-diethoxyphosphinyl)-acetate (11 mmol) in THF (10 ml) is added to a stirred slurry of sodium hydride (12 mmol) in THF (10 ml) at 200° C. After gas evolution has ceased, a solution of aldehyde 3 (10 mmol) in THF (5 ml) is added and stirring is continued overnight. Several milliliters of water are added to decompose excess sodium hydride, and the reaction mixture is partitioned between ethyl acetate (20 ml) and water (20 ml). The aqueous phase is extracted with an additional 10 ml aliquot of ethyl acetate, and the combined organic layers are washed with 30 ml of brine, dried (MgSO₄) and concentrated. The product is purified on a silica gel column, eluting with 40% ethyl acetate in hexane.

Preparation of Saturated Amino Acid 5:

A solution of 4 (18mmol) in ethanol (50 ml) is hydrogenated over 5% palladium on carbon (20 wt. %) with 50 psi of hydrogen for 24 hrs. The reaction mixture is filtered through Celite ™ and the solvent is evaporated to furnish 5.

Procedure for the Synthesis of Tetrazole 6 and final product 7:

A solution of 5 (10 mmol) and azidotributylstannane (20 mmol) is heated to 80° C. for three days. The mixture is cooled to room temperature (24° C.) and treated with 25 ml of methanolic HCl and then concentrated in vacuo. The residue is dissolved in 20 ml of 6N aqueous HCl and extracted with 3×15 ml of ether. The aqueous layer is concentrated in vacuo, dissolved in 40 ml of 6N aqueous HCl, and heated to reflux overnight. After cooling to room temperature, the solution is concentrated in vacuo, dissolved in 15 ml of water and treated with propylene oxide (30 mmol). After heating this mixture at 50° C. for 1 hour the pH is adjusted to 4. The mixture is concentrated in vacuo and then suspended in 50 ml of ethanol and refluxed for 45 minutes. The solid that forms is collected by vacuum filtration, washed with acetone and dried overnight in a vacuum desiccator to furnish 7 as a white solid.

The invention being thus described, it will be obvious that the same may be varied in many ways. Such variations are not to be regarded as a departure from the spirit and scope of the invention and all such modifications are intended to be included within the scope of the claims.

What is claimed is:

1. A method for treating a dysfunction in excitatory amino acid neurotransmission in a mammal, comprising administering an effective amount of the following compound:

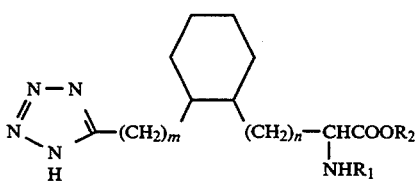

wherein R¹ and R² are selected from the group consisting of hydrogen and C₁ to C₆ alkyl; the stereoisomers being in their resolved or racemic form; n and m are independently 0, 1, 2, or 3; and pharmaceutically acceptable salts thereof;

with a pharmaceutically acceptable carrier.

2. A method for treating a dysfunction in excitatory amino acid neurotransmission in a mammal, comprising administering an effective amount of the following compound:

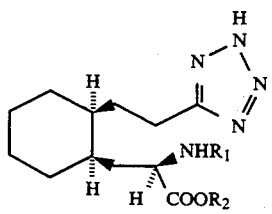

wherein $R^1$ and $R^2$ are selected from the group consisting of hydrogen and $C_1$ and $C_6$ alkyl; the stereochemical configuration of the compound is specified as being of the (2R, 4R, 5S) configuration and pharmaceutically acceptable salts thereof;

with a pharmaceutically acceptable carrier.

3. The method according to claim 1, wherein said treatment is for relieving pain in a mammal.

4. The method according to claim 2, wherein said treatment is for relieving pain in a mammal.

5. The method according to claim 1, wherein said treatment is for treating convulsions in a mammal.

6. The method according to claim 2, wherein said treatment is for treating convulsions in a mammal.

7. The method according to claim 1, wherein said treatment is for enhancing cognition in a mammal.

8. The method according to claim 2, wherein said treatment is for enhancing cognition in a mammal.

9. The method according to claim 1, wherein said treatment is for treating psychosis in a mammal.

10. The method according to claim 2, wherein said treatment is for treating psychosis in a mammal.

11. The method according to claim 1, wherein said treatment is for treating or preventing neurodegeneration associated with excitatory amino acid neurotransmission dysfunction in a mammal in need thereof.

12. The method according to claim 2, wherein said treatment is for treating or preventing neurodegeneration associated with excitatory amino acid neurotransmission dysfunction in a mammal in need thereof.

13. The method according to claim 1, wherein said treatment is for treating cerebral ischemia in a mammal.

14. The method according to claim 2 wherein said treatment is for treating cerebral ischemia in a mammal.

15. The method according to claim 1, wherein said treatment is for treating emesis in a mammal.

16. The method according to claim 2, wherein said treatment is for treating emesis in a mammal.

* * * * *